United States Patent

Dutzmann et al.

[11] Patent Number: 6,153,636
[45] Date of Patent: Nov. 28, 2000

[54] FUNGICIDAL COMPOSITIONS

[75] Inventors: Stefan Dutzmann, Hilden; Heinz-Wilhelm Dehne, Monheim; Karl-Heinz Kuck, Langenfeld; Wilhelm Brandes, Leichlingen; Wolfgang Krämer, Burscheid, all of Germany

[73] Assignee: Bayer Aktiengesellschaft, Leverkusen, Germany

[21] Appl. No.: 09/296,851

[22] Filed: Apr. 22, 1999

Related U.S. Application Data

[62] Division of application No. 08/989,044, Dec. 11, 1997, Pat. No. 5,965,593, which is a division of application No. 08/787,599, Jan. 22, 1997, Pat. No. 5,736,551, which is a division of application No. 08/646,788, May 21, 1996, Pat. No. 5,639,774, which is a division of application No. 08/432,741, May 2, 1995, Pat. No. 5,569,656, which is a division of application No. 08/249,511, May 26, 1994, Pat. No. 5,439,926.

[30] Foreign Application Priority Data

Jun. 2, 1993 [DE] Germany .............. 43 18 285

[51] Int. Cl.$^7$ .................. A01N 43/12; A01N 43/26; A01N 43/50
[52] U.S. Cl. ............................. 514/399; 514/462
[58] Field of Search ...................... 514/399, 462

[56] References Cited

U.S. PATENT DOCUMENTS

| | | | |
|---|---|---|---|
| 4,851,405 | 7/1989 | Kramer et al. | 514/212 |
| 4,931,560 | 6/1990 | Hubele | 544/315 |
| 5,145,856 | 9/1992 | Clough et al. | 514/274 |
| 5,373,013 | 12/1994 | Hubele et al. | 514/225 |

FOREIGN PATENT DOCUMENTS

| | | |
|---|---|---|
| 167 768 | 1/1986 | Germany . |
| 281 842 | 9/1988 | Germany . |
| 3 719 236 | 1/1989 | Germany . |

OTHER PUBLICATIONS

Lyr et al., C.A. vol. 98 (1983) 98:138,975b.
Worthing et al., The Pesticide Manual, 9th Edition (1991) pp. 86, 378–834 and 847.
Worthing et al, "The Pesticide Manual", 9$^{th}$ Ed. (1991) pp. 701 and 702.

*Primary Examiner*—Allen J. Robinson
*Attorney, Agent, or Firm*—Norris, McLaughlin & Marcus, P.A.

[57] ABSTRACT

A novel fungicidal composition comprising a fungicidally effective amount of a combination consisting of
(A) the known aminomethyl heterocycle of the formula

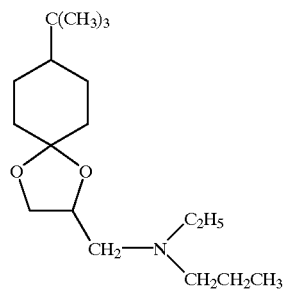

(I)

and
(B) at least one other known fungicidally active compound selected from the group mentioned in the specification.

The novel compositions show a synergistic activity.

3 Claims, No Drawings

FUNGICIDAL COMPOSITIONS

This is a division of application Ser. No. 08/989,044, filed on Dec. 11, 1997, now U.S. Pat. No. 5,965,593, which is a division of application Ser. No. 08/787,599, filed on Jan. 22, 1997, now U.S. Pat. No. 5,736,551, which is a division on application Ser. No. 08/646,788, filed on May 21, 1996, now U.S. Pat. No. 5,639,774, which is a division of application Ser. No. 08/432,741, filed on May 2, 1995, now U.S. Pat. No. 5,569,656, which is a division of application Ser. No. 08/249,511, filed on May 26, 1994, now U.S. Pat. No. 5,439,926.

The present invention relates to novel combinations of active compounds, which combinations consist of the known 8-t-butyl-2-(N-ethyl-N-n-propylamino)-methyl-1,4-dioxaspiro[4.5]decane on the one hand and of further, known, fungicidal active compounds on the other, and are very well suited for controlling fungi.

It is already known that 8-t-butyl-2-(N-ethyl-N-n-propylamino)-methyl-1,4-dioxaspiro[4.5]decane possesses fungicidal properties (cf. EP-OS (European Published Specification) 0 281 842). The activity of this compound is good; however, in many cases it leaves something to be desired when being used in small quantities.

It is also already known that many azole derivatives, aryl benzyl ethers, benzamides, morpholine compounds, and other heterocycles, can be employed for controlling fungi (cf. K. H. Buichel "Pflanzenschutz und Schädlingsbekämpfung" (Plant Protection and the Control of Pests), pages 140–153, Georg Thieme-Verlag, Stuttgart 1977, EP-OS (European Published Specification) 0 040 345, DE-OS (German Published Specification) 2 324 010, DE-OS (German Published Specification) 2 201 063, EP-OS (European Published Specification) 0 112 284, EP-OS (European Published Specification) 0 304 758 and DD-PS (East German Patent Specification) 140 412).

Fungicidal combinations of active compounds consisting of 8-t-butyl-2-(3,5-dimethylpiperidin-1-yl-methyl)-1,4-dioxaspiro[4.5]decane and other known fungicidal active compounds are also known (cf. DE-OS (German Published Specification) 37 19 326).

However, the activity of the known fungicidal active compounds as individual compounds, like that of the known synergistic combinations of active compounds, is however, in particular when small quantities are being used, not always completely satisfactory in all areas of application.

It has now been found that the novel combinations of active compounds consisting of 8-t-butyl-2-(N-ethyl-N-n-propylamino)-methyl-1,4-dioxaspiro[4.5]decane of the formula (I)

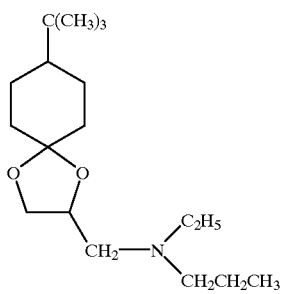
(I)

and at least (1) one azole derivative of the formula

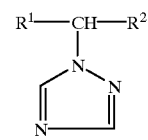
(II)

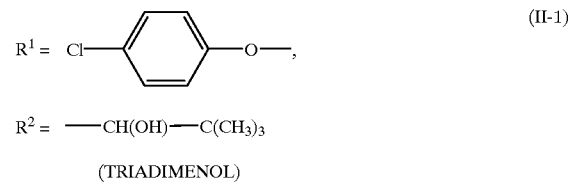
(II-1)
(TRIADIMENOL)

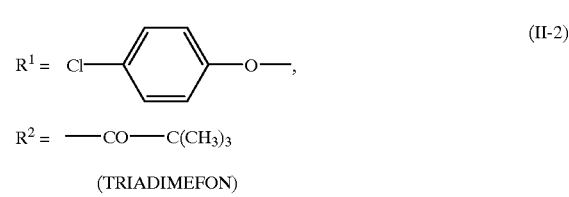
(II-2)
(TRIADIMEFON)

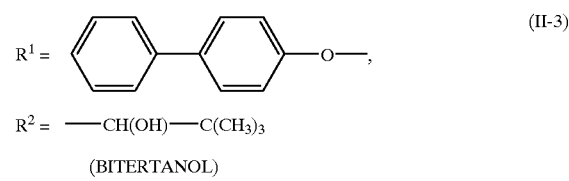
(II-3)
(BITERTANOL)

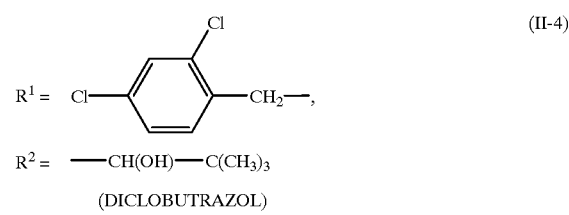
(II-4)
(DICLOBUTRAZOL)

and/or at least (2) one azole derivative of the formula

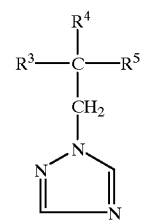
(III)

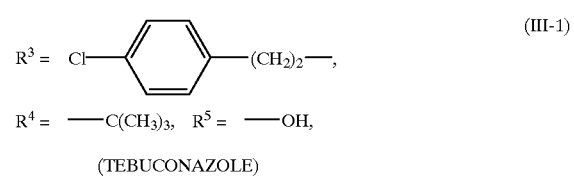
(III-1)
(TEBUCONAZOLE)

-continued
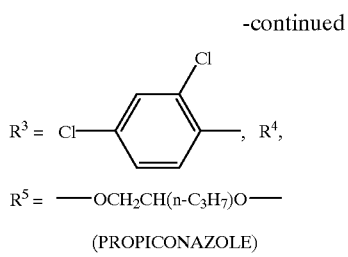
(PROPICONAZOLE) (III-2)
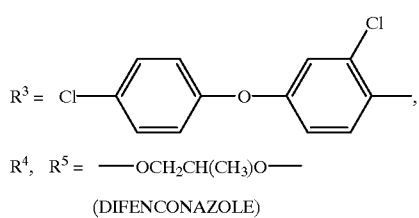
(DIFENCONAZOLE) (III-3)
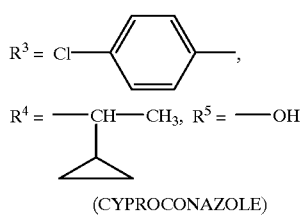
(CYPROCONAZOLE) (III-4)
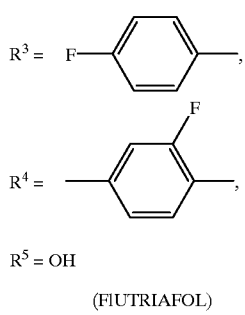
(FlUTRIAFOL) (III-5)
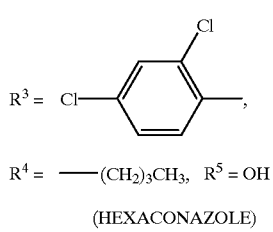
(HEXACONAZOLE) (III-6)
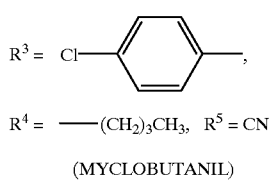
(MYCLOBUTANIL) (III-7)
-continued
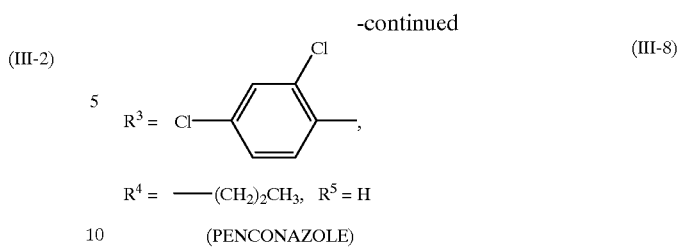
(PENCONAZOLE) (III-8)
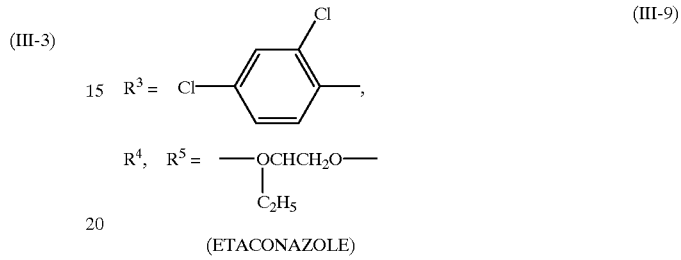
(ETACONAZOLE) (III-9)
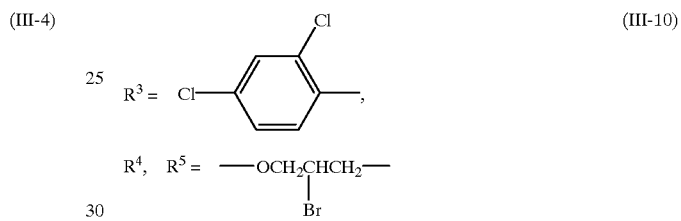
(BROMUCONAZOLE) (III-10)
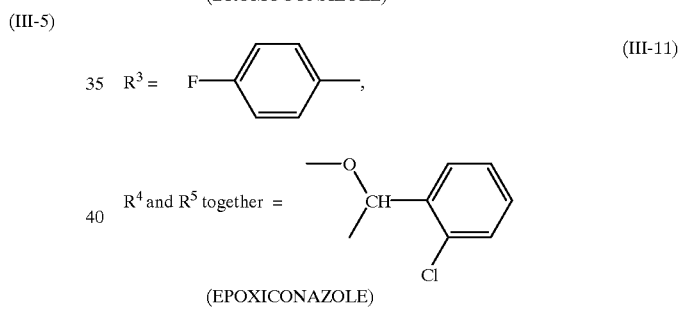
(EPOXICONAZOLE) (III-11)
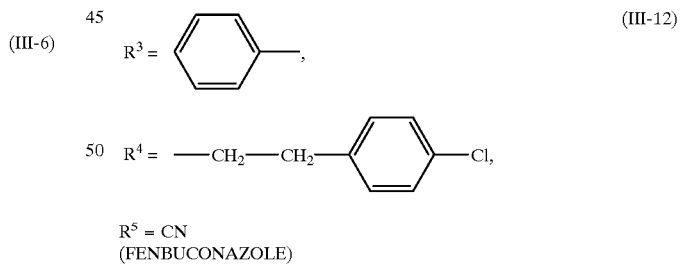
(FENBUCONAZOLE) (III-12)
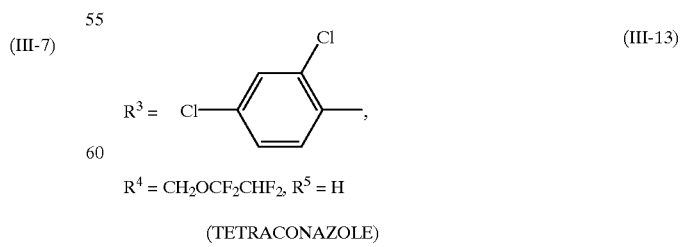
(TETRACONAZOLE) (III-13)
and/or
(3) the azole derivative of the formula -continued

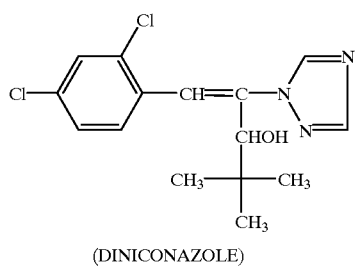

(IV)

(DINICONAZOLE)

and/or
(4) the azole derivative of the formula

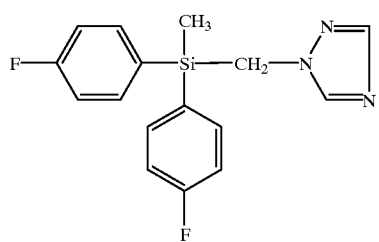

(V)

(FLUSILAZOLE)

and/or
(5) the azole derivative of the formula

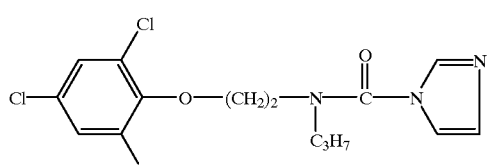

(VI)

(PROCHLORAZ)

and/or
(6) at least one azole derivative of the formula

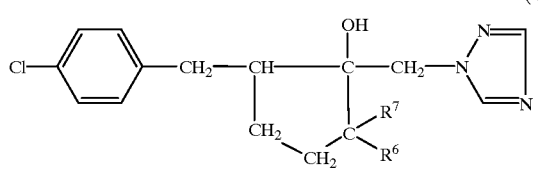

(VII)

$R^6 = CH_3, R^7 = CH_3$ (VII-1)
(METCONAZOLE)
$R^6 = H, R^7 = CH(CH_3)_2$ (VII-2)
(IPCONAZOLE)
and/or
(7) the azole derivative of the formula -continued

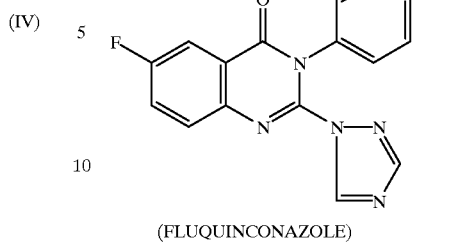

(VIII)

(FLUQUINCONAZOLE)

and/or
(8) at least one of the heterocycles of the formula

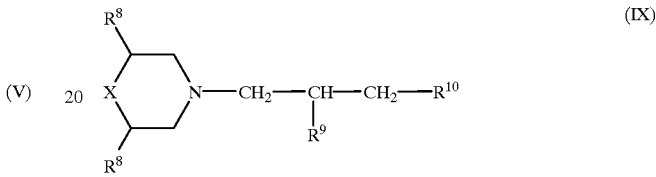

(IX)

$X = O, R^8 = CH_3, R^9 = H, R^{10} = C_{10}H_{21}$ (IX-1)
(TRIDEMORPH)
$X = O, R^8 = CH_3, R^9 = H, R^{10} = C_9H_{19}$ (IX-2)
(ALDIMORPH)

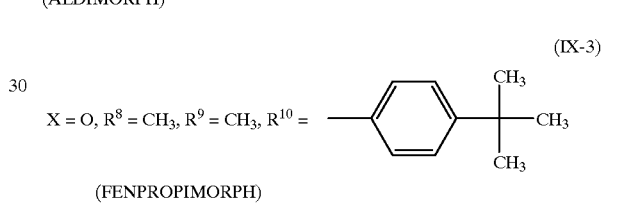

(IX-3)

$X = O, R^8 = CH_3, R^9 = CH_3, R^{10} =$ (FENPROPIMORPH)

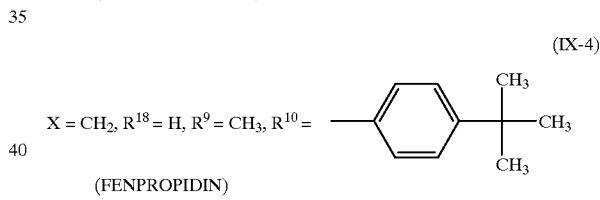

(IX-4)

$X = CH_2, R^{18} = H, R^9 = CH_3, R^{10} =$ (FENPROPIDIN)

and/or
(9) the compound of the formula

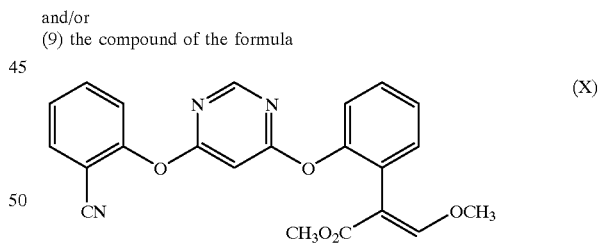

(X)

and/or
(10) the compound of the formula

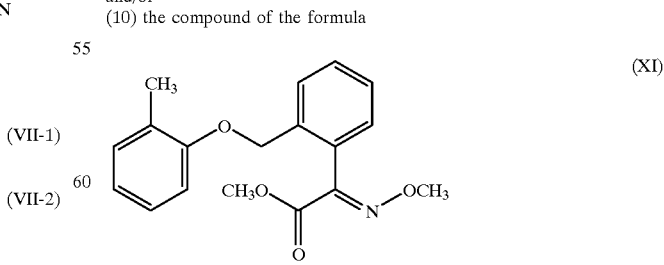

(XI)

and/or
(11) the compound of the formula

-continued

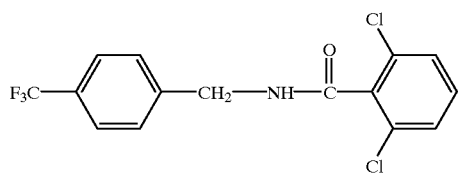
(XII)

and/or
(12) the compound of the formula

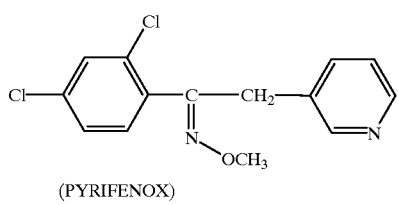<br>(PYRIFENOX)
(XIII)

and/or
(13) the compound of the formula

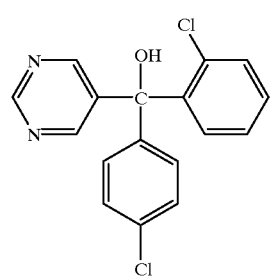<br>(FENARIMOL)
(XIV)

and/or
(14) the compound of the formula

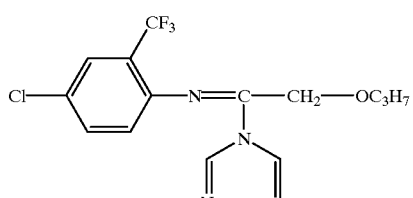<br>(TRIFLUMIZOLE)
(XV)

and/or
(15) at least one of the compounds of the formula

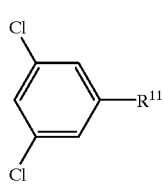
(XVI)

$R^{11} =$ 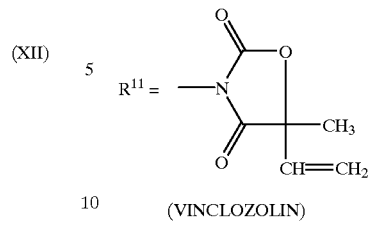 (XVI-1)

(VINCLOZOLIN)

$R^{11} =$ 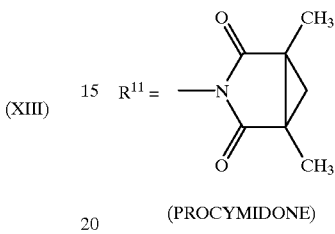 (XVI-2)

(PROCYMIDONE)

$R^{11} =$ 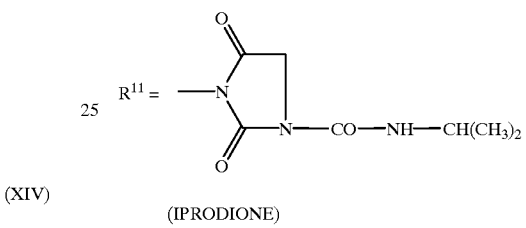 (XVI-3)

(IPRODIONE)

and/or
(16) at least one of the compounds of the formula

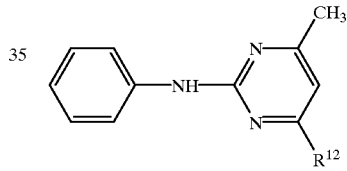 (XVII)

 (XVII-1)
(PYRIMETHANIL)
 (XVII-2)
(MEPANIPYRIM)

$R^{12} =$ 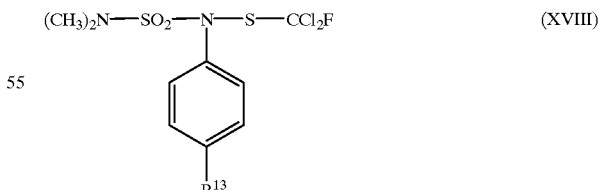 (XVII-3)

(CYPRODINYL)

and/or
(17) at least one of the compounds of the formula

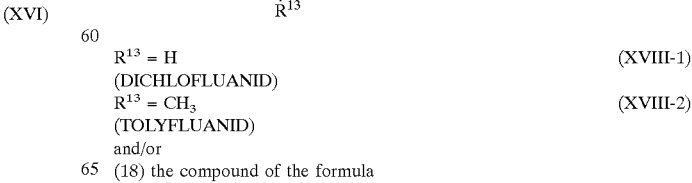 (XVIII)

$R^{13} = H$ (XVIII-1)
(DICHLOFLUANID)
$R^{13} = CH_3$ (XVIII-2)
(TOLYFLUANID)
and/or
(18) the compound of the formula -continued

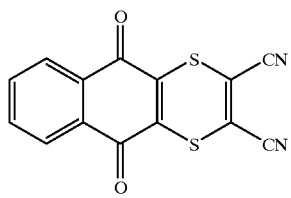

(DITHIANON)

and/or
(19) the compound of the formula

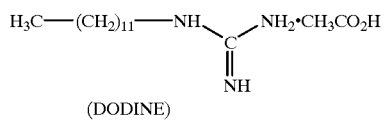   (XX)

(DODINE)

and/or
(20) the compound of the formula

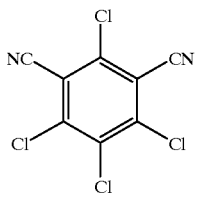   (XXI)

(CHLOROTHALONIL)

and/or
(21) the compound of the formula

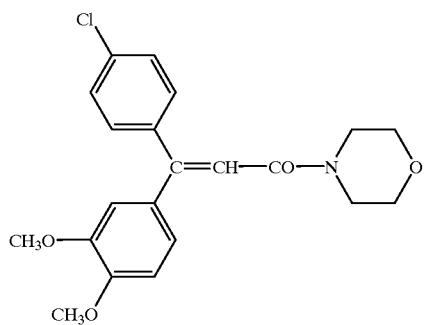   (XXII)

(DIMETHOMORPH)

and/or
(22) the compound of the formula

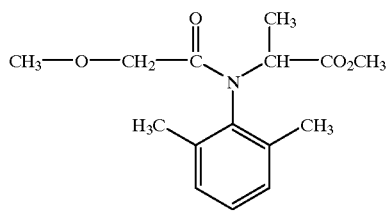   (XXIII)

(METALAXYL)

and/or
(23) the compound of the formula

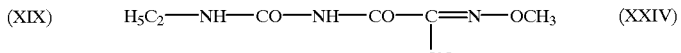   (XXIV)

(CYMOXANIL)

and/or
(24) the compound of the formula

   (XXV)

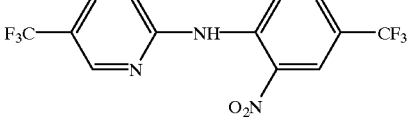

(FLUAZINAM)

and/or
(25) the compound of the formula

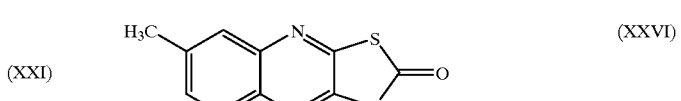   (XXVI)

and/or
(26) at least one of the compounds of the formula
$Cl_3C-S-R^{14}$   (XXVII)

   (XXVII-1)

$R^{14} = $ (CAPTAN)

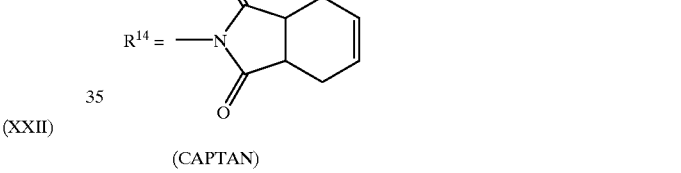   (XXVII-2)

$R^{14} = $ (FOLPET)

and/or
(27) the compounds of the formulae
$3\ Cu(OH)_2 \cdot CuCl_2 \cdot x\ H_2O$   (XXVIII-1)
and

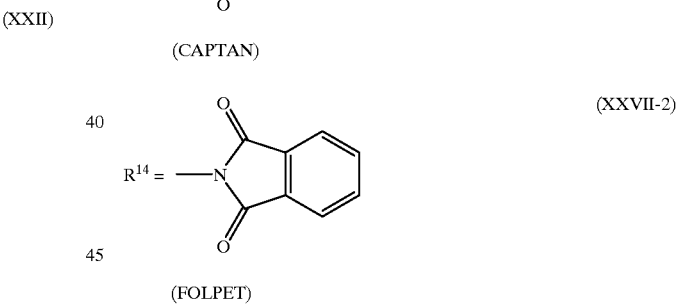   (XXVIII-2)

(COPPEROXINAT)

and/or
(28) the compound of the formula

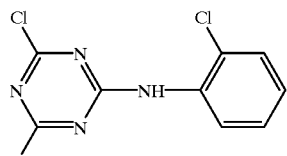

(ANILAZINE)

and/or
(29) the compound of the formula

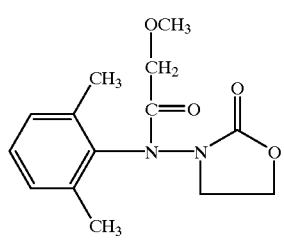

(OXADIXYL)

and/or
(30) the compound of the formula

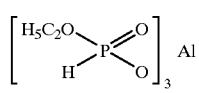

(FOSETYL AL)

and/or
(31) the compound of the formula

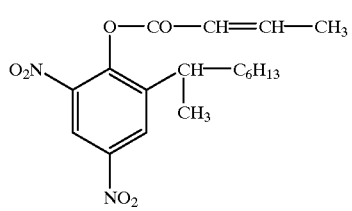 (XXXII)

(DINOCAP)

and/or
(32) the compound of the formula

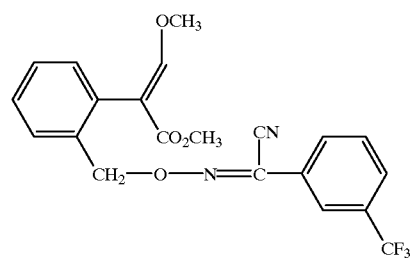 (XXXIII)

and/or
(33) the compounds of the formula

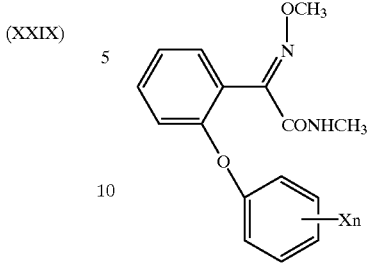 (XXIX)

X = F, Cl, Br, $CH_3$
n = 0, 1, 2, 3
and/or
(34) the compound of the formula

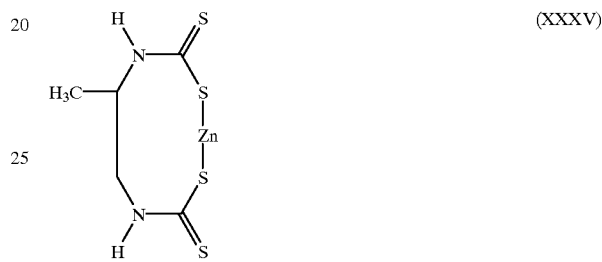 (XXXV)

(PROPINEB)

and/or
(35) at least one of the compounds of the formula

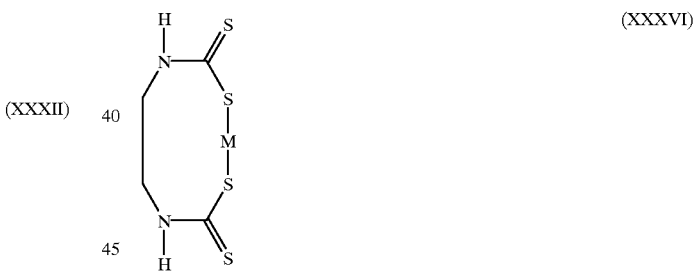 (XXXVI)

| M = Zn | (XXXVI-1) |
|---|---|
| (ZINEB) | |
| M = Mn | (XXXV)-2 |
| (MANEB) | |
| (XXXVI-3) = Mixture of (XXXVI-1) and (XXXVI-2) | |
| (MANCOZEB) | | and/or
(36) one compound of the formula

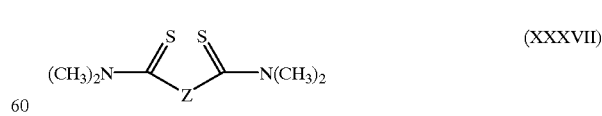 (XXXVII)

| Z = —S—S— (THIRAM) | (XXXVII-1) |
|---|---|
| / = —S—Zn—S— (ZIRAM) | (XXXVII-2) | and/or
(37) the compound of the formula

-continued

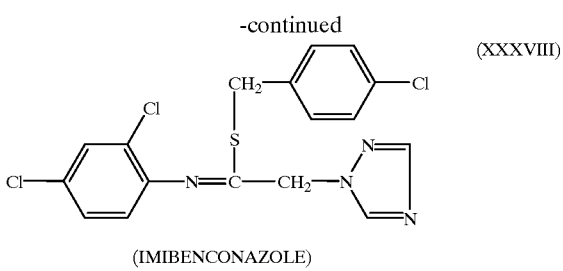

(XXXVIII)

(IMIBENCONAZOLE)

and/or
(38) the compound of the formula

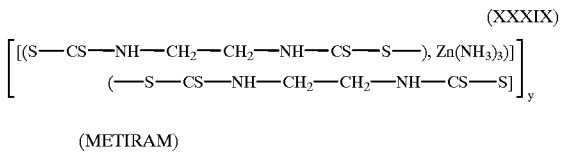

(XXXIX)

(METIRAM)

and/or
(39) the compound of the formula

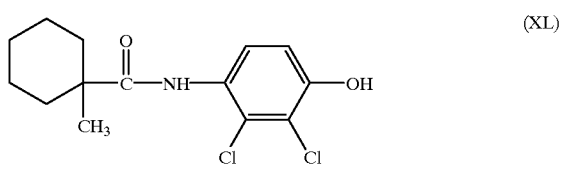

(XL)

and/or
(40) the compound of the formula

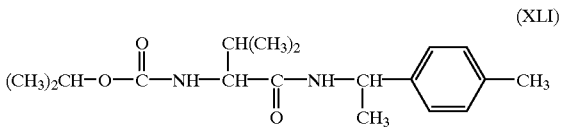

(XLI)

and/or
(41) the compound of the formula
$S_x$
(WETTABLE SULPHUR)
and/or
(42) at least one of the compounds of the formula

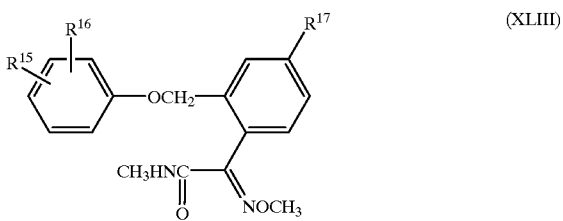

(XLII)

(XLIII)

in which
$R^{15}$ and $R^{16}$, independently of each other, represent hydrogen, halogen, methyl or phenyl, and
$R^{17}$ represents hydrogen or methyl,
possess very good fungicidal properties.

Surprisingly, the fungicidal effect of the combinations of active compounds according to the invention is appreciably higher than the sum of the effects of the individual active compounds and also appreciably higher than the effects of the known combinations of active compounds. There thus exists a synergistic effect which could not have been foreseen, and not simply a supplementation of the effect.

8-t-Butyl-2-(N-ethyl-N-n-propylamino)-methyl-1,4-dioxaspiro [4.5]decane of the formula (I), and its employment as a fungicide, are known (cf. EP-OS (European Published Specification) 0 281 842).

The fungicidal components which are also present in the combinations of active compounds according to the invention are likewise known. The active compounds are described in detail in the following publications:
(1) compounds of the formula (II)
   DE-OS (German Published Specification) 2 201 063
   DE-OS (German Published Specification) 2 324 010
   DE-OS (German Published Specification) 2 737 489
(2) compounds of the formula (III)
   DE-OS (German Published Specification) 3 018 866
   DE-OS (German Published Specification) 2 551 560
   EP 47 594
   DE 2 735 872
(3) compound of the formula (IV)
   DE-OS (German Published Specification) 28 38 847
(4) compound of the formula (V)
   EP 68 813
   U.S. Pat. No. 4,496,551
(5) compound of the formula (VI)
   DE-OS (German Published Specification) 2 429 523
   DE-OS (German Published Specification) 2 856 974
   U.S. Pat. No. 4,108,411
(6) compounds of the formula (VII)
   EP 329 397
(7) Compound of the formula (VIII)
   EP 183 458
(8) compounds of the formula (IX)
   DD 140 041
(9) compound of the formula (X)
   EP 382 375
(10) compound of the formula (XI)
   EP 515 901
(11) compound of the formula (XII)
   EP 314 422
(12) compound of the formula (XIII)
   EP 49 854
(13) compound of the formula (XIV)
   DE-OS (German Published Specification) 1 770 288
   U.S. Pat. No. 3,869,456
(14) compound of the formula (XV)
   DE 2 814 041
(15) compounds of the formula (XVI)
   DE 2 207 576
   U.S. Pat. No. 3,903,090
   U.S. Pat. No. 3,755,350
   U.S. Pat. No. 3,823,240
(16) compounds of the formula (XVII)
   EP 270 111 and
   EP 310 550
(21) compound of the formula (XXII)
   EP 219 756
(37) compound of the formula (XXXVIII)
   U.S. Pat. No. 4 512 989
(42) compounds of the formula (XLIII)
   EP 398 692

Compounds from the groups (17), (18), (19), (20), (25), (26), (27), (28), (31), (34), (35), (36) and (41) are described, for example, in K. H. Büchel, "Pflanzenschutz und Schädlingsbekämpfung (Plant Protection and the Control of Pests), pages 121–153, Georg Thieme-Verlag, Stuttgart, 1977.

In addition to the active compound of the formula (I), the combinations of active compounds according to the invention contain at least one active compound from the compounds of the groups (1) to (42). In addition to this, they can also contain further fungicidally active admixed components.

The synergistic effect is particularly apparent when the active compounds in the combinations of active compounds according to the invention are present in particular ratios by weight. However, the ratios by weight of the active compounds in the combinations of active compounds can be varied within a relatively wide range. In general 0.1 to 10 parts by weight, preferably 0.3 to 3 parts by weight, of at least one active compound from the groups (1) to (42) is/are allocated to 1 part by weight of active compound of the formula (I).

The combinations of active compounds according to the invention possess very good fungicidal properties. They can be employed, in particular, for controlling phytopathogenic fungi, such as Plasmodiophoromycetes, Oomycetes, Chytridiomycetes, Zygomycetes, Ascomycetes, Basidiomycetes, Deuteromycetes, etc.

The combinations of active compounds according to the invention are particularly suited for controlling cereal diseases, such as Erysiphe, Cochliobolus, Septoria, Pyrenophora and Leptosphaeria, and for use against fungal infestation of vegetables, grapes and fruit, for example against Venturia or Podosphaera on apples, Uncinula on vine plants or Sphaerotheca on cucumbers.

The high level of tolerance by plants of the combinations of active compounds in the concentrations which are necessary for controlling plant diseases makes it possible to treat above-ground parts of plants, plant material and seeds, and the soil.

The combinations of active compounds according to the invention can be converted into the customary formulations, such as solutions, emulsions, suspensions, powders, foams, pastes, granules, aerosols, very fine capsules in polymeric substances and in coating compositions for seeds, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The combinations of active compounds according to the invention can be present in the formulations as a mixture with other known active compounds, such as fungicides, insecticides, acaricides and herbicides, and in mixtures with fertilizers or plant growth regulators.

The combinations of active compounds can be used as such or in the form of their formulations or the use forms prepared therefrom, such as ready-to-use solutions, emulsifiable concentrates, emulsions, suspensions, wettable powders, soluble powders and granules.

They are used in a customary manner, for example by watering, spraying, atomizing, scattering, brushing on, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seeds, amounts of active compound of 0.001 to 50 g per kilogram of seeds, preferably 0.01 to 10 g, are generally required.

For the treatment of the soil, active compound concentrations of 0.00001 to 0.1% by weight, preferably of 0.0001 to 0.02% by weight, are required at the site of action.

The good fungicidal effect of the combinations of active compounds according to the invention is evident from the examples below. While the individual active compounds or the known combinations of active compounds exhibit deficiencies in their fungicidal effect, it is clearly evident from the tables of the following examples that the effect of the combinations of active compounds according to the invention which has been found is greater than the sum of the effects of the individual active compounds and also greater than the effects of the known combinations of active compounds.

EXAMPLE 1

Erysiphe Test (wheat)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of powdery mildew pustules.

Evaluation is carried out 7 days after the inoculation.

The active compounds, active compound concentrations and experimental results are shown in the following table.

TABLE 1

Erysiphe test (wheat)/protective

| Active compound | Active compound concentration in the spray liquor in ppm | Degree of effect in % of the untreated control |
|---|---|---|
| known: | | |
| (H₃C)₃C—[cyclohexane-spiro-dioxolane]—CH₂—N(CH₂CH₃)(CH₂CH₂CH₃) (I) | 2 | 59 |
| Cl—C₆H₄—O—CH(triazolyl)—CH(OH)—C(CH₃)₃ (II-1) | 2 | 75 |
| mixture according to the invention | | |
| (I) + (II-I) 3:1 | 1.5 + 0.5 | 100 |

EXAMPLE 2

Erysiphe Test (barley)/curative
Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.* sp. *hordei*. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

The active compounds, active compound concentrations and experimental results are shown in the following table.

TABLE 2

Erysiphe test (barley)/curative

| Active compound | Active compound concentration in g/ha | Degree of effect in % of the untreated control |
|---|---|---|
| known: | | |
| (CH₃)₃C—[cyclohexane-spiro-dioxolane]—CH₂—N(CH₂CH₃)(CH₂CH₂CH₃) (I) | 40<br>20<br>12 | 88<br>75<br>66 |

TABLE 2-continued
Erysiphe test (barley)/curative
| Active compound | Active compound concentration in g/ha | Degree of effect in % of the untreated control |
|---|---|---|
| 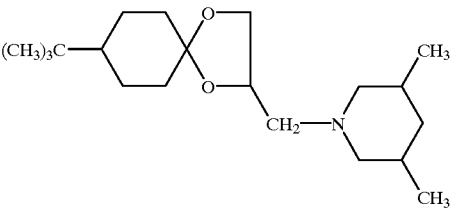 | 40<br>20<br>12 | 100<br>79<br>59 |
| 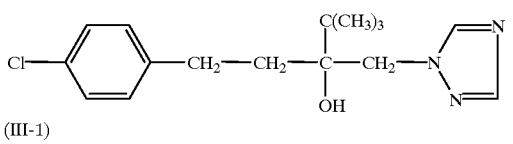<br>(III-1) | 40 | 96 |
| 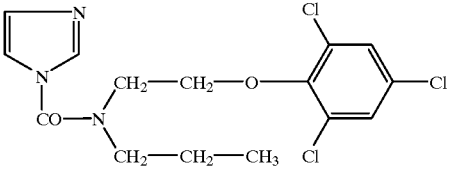<br>(VI) | 12 | 50 |
| 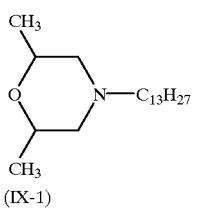<br>(IX-1) | 20 | 25 |
| 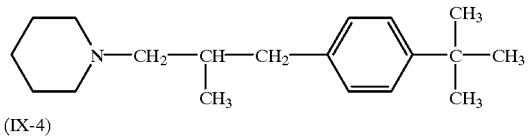<br>(IX-4) | 20 | 79 |
| 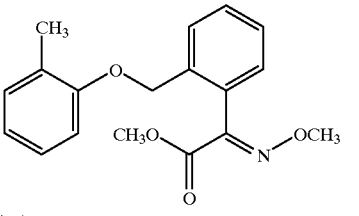<br>(XI) | 40 | 88 |
| <br>(X) | 20 | 63 |
known mixtures from DE-OS TABLE 2-continued Erysiphe test (barley)/curative

| Active compound | Active compound concentration in g/ha | Degree of effect in % of the untreated control |
|---|---|---|
| (German Published Specification) 37 19 326 | | |
| (CH$_3$)$_3$C—[cyclohexane-dioxolane]—CH$_2$—N[piperidine with 3,5-diCH$_3$] + (III-1)  1:1 | 20 + 20 | 96 |
| (CH$_3$)$_3$C—[cyclohexane-dioxolane]—CH$_2$—N[piperidine with 3,5-diCH$_3$] + (II-1)  5:1 | 10 + 2 | 66 |
| mixtures according to the invention | | |
| (I) + (III-1) 1:1 | 20 + 20 | 100 |
| (I) + (II-1) 5:1 | 10 + 2 | 84 |
| (I) + (VI) 5:1 | 10 + 2 | 84 |
| (I) + (IX-1) 1:1 | 10 + 10 | 79 |
| (I) + (IX-4) 1:1 | 10 + 10 | 88 |
| (I) + (XI) 1:1 | 20 + 20 | 100 |
| (I) + (X) 1:1 | 10 + 10 | 84 |
| (I) + (III-4) 5:1 | 20 + 4 | 96 |
| (I) + (III-4) 1:1 | 10 + 2 | 79 |
| (I) + (VI) 1:1 | 20 + 20 | 100 |
| (I) + (III-2) 5:1 | 20 + 4 | 88 |
| (I) + (XI) 5:1 | 10 + 2 | 79 |
| (I) + (X) 5:1 | 20 + 4 | 75 |

EXAMPLE 3

Erysiphe Test (wheat)/curative

Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f. sp. tritici. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

The active compounds, active compound concentrations and experimental results are shown in the following table.

TABLE 3
Erysiphe test (wheat)/curative
| Active compound | Active compound concentration in g/ha | Degree of effect in % of the untreated control |
|---|---|---|
| known: | | |
| 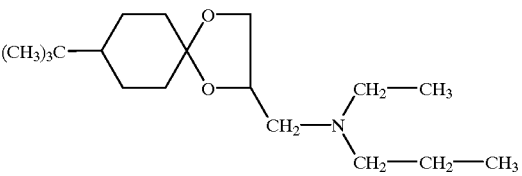 (I) | 40<br>20 | 73<br>73 |
| 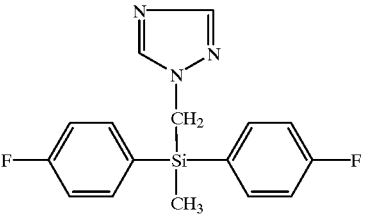 (V) | 40 | 73 |
| 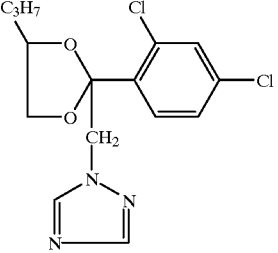 (III-2) | 20 | 55 |
| 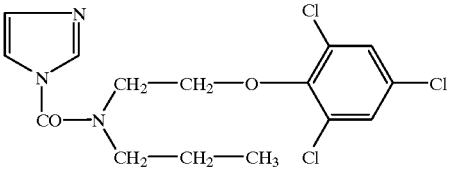 (VI) | 40 | 77 |
| 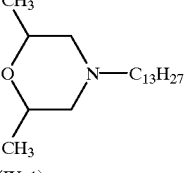 (IX-1) | 40 | 82 |
| mixtures according to the invention | | |
| (I) + (V)<br>1:1 | 20 + 20 | 100 |
| (I) + (VI)<br>1:1 | 20 + 20 | 90 |
| (I) + (III-2)<br>1:1 | 10 + 10 | 86 |

TABLE 3-continued

Erysiphe test (wheat)/curative

| Active compound | Active compound concentration in g/ha | Degree of effect in % of the untreated control |
|---|---|---|
| (I) + (IX-1) 1:1 | 20 + 20 | 90 |
| (I) + (IX-3) 1:1 | 20 + 20 | 100 |

EXAMPLE 4

Erysiphe Test (wheat)/protective

Solvent: 10 parts by weight of N-methyl-pyrrolidone
Emulsifier: 0.6 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of powdery mildew pustules.

Evaluation is carried out 7 days after the inoculation.

The active compounds, active compound concentrations and experimental results are shown in the following table.

TABLE 4

Erysiphe test (wheat)/protective

| Active compound | Active compound concentration in g/ha | Degree of effect in % of the untreated control |
|---|---|---|
| known: | | |
| 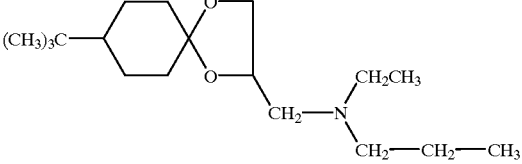 (I) | 40 12 | 75 11 |
| 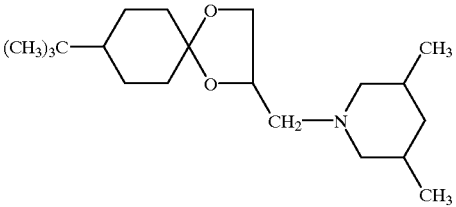 | 40 12 | 75 60 |
| 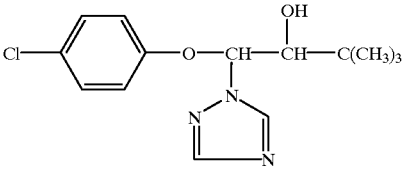 (II-1) | 40 | 70 |

TABLE 4-continued

Erysiphe test (wheat)/protective

| Active compound | Active compound concentration in g/ha | Degree of effect in % of the untreated control |
|---|---|---|
| known: | | |
| 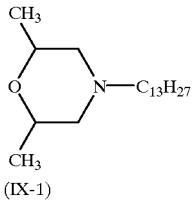 (IX-1) | 12 | 30 |
| 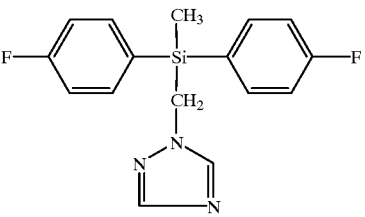 (V) | 20 | 40 |
| known mixture from DE-OS (German Published Specification) 37 19 326 | | |
| (CH₃)₃C—⟨cyclohexyl-dioxolane⟩—CH₂—N⟨dimethylpiperidine⟩ + (II-1) | 20 + 20 | 75 |
| mixtures according to the invention | | |
| (I) + (II-1) 1:1 | 20 + 20 | 85 |
| (I) + (IX-1) 5:1 | 10 + 2 | 70 |
| (I) + (V) 1:1 | 10 + 10 | 90 |

EXAMPLE 5

Podosphaera Test (apple)/protective

Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew *Podosphaera leucotricha*.

The plants are then placed in a greenhouse at 23° C. and a relative atmospheric humidity of about 70%.

Evaluation is carried out 10 days after the inoculation.

Active compounds, active compound concentrations and experimental results are shown in the following table.

TABLE 5

Podosphaera test (apple)/protective

| Active compound | Active compound concentration in ppm | Degree of effect in % of the untreated control |
|---|---|---| known:

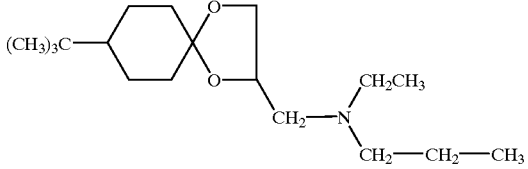

(I)

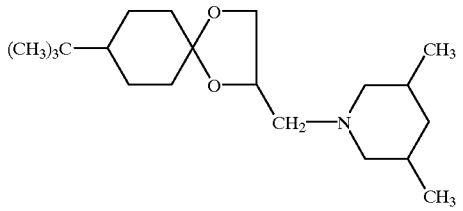

(II-1)

known from DE-OS 37 19 326:

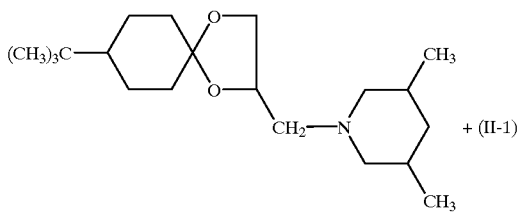

5:1

| | (5:1)<br>0.5 + 0.1 | 55 | mixture according to the invention:

| (I) + (II-1)<br>5:1 | 0.5 + 0.1 | 86 |

It is understood that the specification and examples are illustrative but not limitative of the present invention and that other embodiments within the spirit and scope of the invention will suggest themselves to those skilled in the art.

What is claimed is:

1. A fungicidal composition comprising a synergistic fungicidally effective amount of a combination of:

(A) 8-t-butyl-2-(N-ethyl-N-n-propylamino)-methyl-1,4-dioxaspiro[4.5]-decane of the formula

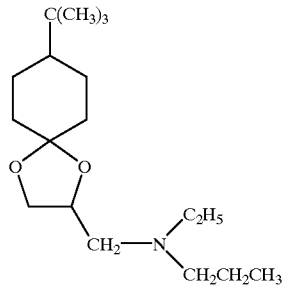

(I)

and (B) a compound of the formula

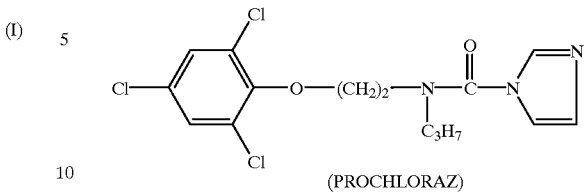

(PROCHLORAZ)

wherein the weight ratio of (A):(B) is between about 1:0.1 and 1:10.

2. A composition according to claim 1, wherein the weight ratio of (A):(B) is between about 1:0.3 and 1:3.

3. A method of combating fungi which comprises administering to such fungi or to a fungus habitat a synergistic fungicidally effective amount of a composition according to claim 1.

* * * * *